United States Patent [19]

Voege et al.

[11] Patent Number: 4,666,939

[45] Date of Patent: May 19, 1987

[54] STABILIZED ANTHELMINTIC FORMULATIONS

[75] Inventors: Herbert Voege; Hubert Rast, both of Leverkusen, Fed. Rep. of Germany

[73] Assignee: Bayer Aktiengesellschaft, Leverkusen, Fed. Rep. of Germany

[21] Appl. No.: 713,962

[22] Filed: Mar. 20, 1985

[30] Foreign Application Priority Data

Mar. 29, 1984 [DE] Fed. Rep. of Germany ....... 3411627

[51] Int. Cl.⁴ ............................................. A61K 31/27
[52] U.S. Cl. .................................... 514/482; 514/970
[58] Field of Search ................................ 514/482, 970

[56] References Cited

U.S. PATENT DOCUMENTS 4,032,655 6/1977 Kolling et al. ...................... 514/482

*Primary Examiner*—Frederick E. Waddell
*Attorney, Agent, or Firm*—Sprung Horn Kramer & Woods

[57] ABSTRACT

A stabilized febantel formulation comprising febantel, a water-miscible organic diluent and an acid, base or buffer salt in an amount such that when diluted 1:10 with water the formulation has a pH value of about 3 to 5. The formulation is far more stable than in the absence of the acid, base or buffer salt.

7 Claims, No Drawings

STABILIZED ANTHELMINTIC FORMULATIONS

The present invention relates to stabilized anthelmintic formulations of febantel, their preparation and their use.

Febantel, (N-{2-[2,3-bis-(methoxycarbonyl)-guanidino]5-(phenylthio)-phenyl}-2-methoxyacetamide) is used as a medicament for combating various worms in animals. It is employed, for example, in the form of suspensions, granules, powders or tablets. Of particular interest, however, are formulations in which the active compound is present in dissolved form, and which either can be injected or can be applied onto the skin as solutions. The latter formulations are frequently called pour-on or spot-on formulations.

The problem associated with the desired solutions is that the active compound is not very chemically stable in dissolved form. The solvents are always organic solvents which may or may not contain water, since the active compound is virtually insoluble in water alone.

It has now been found that formulations of febantel based on water-miscible organic diluents can be stabilized by a method in which the pH value of the formulation diluted 1:10 with water is determined, and the amount of a base, acid or buffer substance required to establish a pH value of about 3–5 is added to the formulation.

The invention relates to formulations of febantel which have been stabilized by this method, and the process for their preparation.

Examples of organic water-miscible solvents which may be mentioned as solvents for febantel are ether-alcohols, such as glycerol formal or 2-dimethyl-4-oxymethyl-1,3-dioxalan, heterocyclic compounds, such as N-Methyl-pyrrolidone, esters, such as dimethyl sulphoxide or ethyl lactate, and ester-amides, such as dimethylacetamide.

Less water-miscible solvents, such as benzyl alcohol, benzyl benzoate or phenyl ethanol, can also be used, alone or as a mixture with the abovementioned solvents.

The water content of the solvents should be <3%, preferably <1%.

The concentration of the active compound in the solvent is 1–20% by weight, preferably 2–15%, particularly preferably 5–10%.

The formulation can contain further customary formulating auxiliaries, such as preservatives, surface-active substances, spreading agents, flavoring substances, dyestuffs or stabilizers.

Spreading agents are understood as being those oily liquids which are particularly easily distributed over the skin. They are known as such in the cosmetics sector. According to a proposal by R. Keymer, Pharm. Ind. 32, 577 (1970), they can be characterized by, for example, their surface tension against air, which should be less than 30 dyn/cm according to the above reference. This spreading can also be determined experimentally on human skin, by the so-called dabbing test (for example in R. Keymer, Pharm. Ind. 32, 577 (1970), or F. Neuwald, K. E. Fetting and A. Szakall, Fette-Seifen-Anstrichmittel 64, 465 (1962).

Suitable spreading agents are virtually all substances which have the properties stated above. The following compounds or classes of compounds are particularly suitable:

Silicone oils of various viscosities

Fatty acid esters, such as ethyl stearate, di-n-butyl adipate, hexyl laurate, dipropylene glycol pelargonate, esters of a branched fatty acid of medium chain length with saturated $C_{16}$–$C_{18}$-fatty alcohols, isopropyl myristate, isopropyl palmitate, caprylic/caproic acid esters of saturated fatty alcohols having a chain length of $C_{12}$–$C_{18}$, isopropyl stearate, oleyl oleate, decyl oleate, ethyl oleate, ethyl lactate, wax-like fatty acid esters, such as synthetic fat similar to that obtained from the duck uropygial gland, dibutyl phthalate, diisopropyl adipate, ester mixtures related to the latter, and others.

Triglycerides, such as caprylic/caproic acid triglyceride, triglyceride mixtures with vegetable fatty acids having a chain length of $C_8$–$C_{12}$ or other specially selected natural fatty acids, partial glyceride mixtures of saturated or unsaturated fatty acids which may furthermore contain hydroxyl groups, monodiglycerides of $C_8$/$C_{10}$-fatty acids, and others.

Fatty alcohols, such as isotridecyl alcohol, 2-octyldodecanol, cetstearyl alcohol or oleyl alcohol.

Fatty acids, such as, for example, oleic acid.

Particularly suitable spreading oils are the following: isopropyl myristate, isopropyl palmitate, caprylates/caproates of saturated fatty alcohols having a chain length of $C_{12}$–$C_{18}$, wax-like fatty acid esters, such as synthetic fat similar to that obtained from duck uropygial gland, and silicone oils.

Preservatives which may be mentioned are benzyl alcohol, hydroxybenzoates, such as the methyl or propyl ester, benzoic acid, chlorobutanol and phenylethyl alcohol.

Other suitable auxiliaries are: adhesion promoters, for example carboxymethylcellulose, methylcellulose and other cellulose and starch derivatives, polyacrylates, alginates, gelatines, gum arabic, polyvinylpyrrolidone, polyvinyl alcohol, copolymers of methyl vinyl ether and maleic anhydride, polyethylene glycols, paraffins, oils, waxes and hydrogenated castor oil.

Colloidal silica or mixtures of the substances listed.

Surface-active substances may also be mentioned, such as, for example, 1. anionic substances, such as Na laurylsulphate, fatty alcohol ether-sulphates, mono- and dialkylpolyglycol ether orthophosphate monoethanolamine salt, 2. cationic substances, such as cetyltrimethylammonium chloride, 3. ampholytic substances, such as di-Na N-lauryl-:-iminodipropionate or lecithin, and 4. non-ionic substances, for example polyoxyethylated castor oil, polyoxyethylated sorbitan monooleate, sorbitan monostearate, ethyl alcohol, glycerol monostearate, polyoxyethylene stearate and alkylphenol polyglycol ethers.

The neutralization can be carried out using bases which form physiologically tolerated salts. The following may be mentioned as bases: ammonia, amines (primary, secondary and tertiary), such as methylamine, ethylamine, ethanolamine, diethanolamine or triethanolamine, basic aminoacids, such as lysine, choline or arginine, and 2-amino-2-hydroxymethyl-1,3-propanediol and N-methylglucamine, and furthermore with inorganic bases, such as NaOH or KOH.

The neutralization can be carried out using acids which form physiologically tolerated salts. The following may be mentioned as acids: inorganic acids, such as hydrohalic acids, for example hydrochloric acid, and sulphuric acid and phosphoric acid, and furthermore organic acids, such as acetic acid, propionic acid, citric acid, lactic acid, ascorbic acid, benzoic acid or salicylic acid.

The neutralization can also be effected by adding buffer substances. Compounds which may be mentioned as such substances are salts of the abovementioned bases with strong acids, such as a hydrohalic acid, sulphuric acid, phosphoric acid, acetic acid or citric acid.

Sodium acetate and citrates may be preferably mentioned.

To carry out the process according to the invention, the desired formulation is advantageously prepared in a customary manner. One part of formulation is then diluted with 10 parts of water, and the pH value of the mixture is measured using a glass electrode. An acid, a base or a buffer salt is then added to the original formulation in an amount such that an aqueous mixture which likewise is diluted 1:10 reaches a pH value of about 3 to 5, measured under the same conditions.

However, it is also possible, using the method described above, first to bring the solvent or the mixture of formulation auxiliaries to the desired pH value and then to add the desired amount of active compound.

The formulations according to the invention have a good and broad action against the following nematodes and cestodes:

1. Hookworms (for example *Uncinaria stenocephala, Ancylostoma caninum* and *Bunostomum trigonocephalum*)
2. Trichostrongylides (for example *Nippostrongylus muris, Haemonchus contortus, Trichostrongylus colubriformis* and *Ostertagia circumcinct*
3. Strongylides (for example *Oesophagostomum columbianum*)
4. Rhabditides (for example *Strongyloides ratti*)
5. Ascarides (for example *Ascaris suum, Toxocara canis* and *Toxascaris leonina*),
6. Thread-worms (for example *Aspiculuris tetraptera*),
7. Heterakides (for example *Heterakis spumosa*),
8. Whip worms (for example *Trichuris muris*),
9. Filariae (for example *Litomosoides carinii* and *Dipetalonema witei*),
10. Cestodes (for example *Hymenolepis nana, Taenia pisiformis* and *Echinococcus multilocularis*)

EXAMPLE 1

5 g of febantel were dissolved in 100 ml of glycerol formal, and the solution was adjusted with acetic acid so that, when 1 part of formulation was diluted with 10 parts of water, a pH value of 4 resulted. The initial content of febantel in the solution prepared in this manner was determined, and the content was determined once again after storage for 3 months at 35° C.

After 3 months, the stabilized solution still contains 4.3% of febantel.

An unstabilized solution stored under the same conditions contained only 0.7% of febantel.

EXAMPLE 2

5.0 g of febantel, 3.0 g of benzyl alcohol, 1.0 g of lactic acid and 95.28 g of N-methylpyrrolidone are weighed out, combined, and stirred until a clear solution is formed. 104.28 g of solution are equivalent to 100 ml. When the solution was diluted 1:10 with water, a pH value of 3.5 resulted. After storage for 3 months at 35° C., the solution still contained 4.2% of active compound. An unstabilized solution stored under the same conditions contained only 1% of active compound after this period.

EXAMPLE 3

10.0 g of febantel are dissolved in 99.0 g of dimethyl sulphoxide to give 100 ml. 0.5 g of citric acid and 0.2 g of trimethanolamine are added to the solution, and are dissolved while stirring. When a sample is diluted with water in a ratio of 1:10, a pH value of 4.2 results.

After storage for 3 months at 35° C., the content of this sample is 85% of the initial value, whereas the content of the unbuffered solution is only 50% of the initial value.

It will be understood that the specification and examples are illustrative but not limitative of the present invention and that other embodiments within the spirit and scope of the invention will suggest themselves to those skilled in the art.

We claim:

1. A stabilized febantel formulation comprising 1 to 20% by weight of febantel, a water-miscible organic diluent, less than 3% of water, and an acid, base or buffer salt in an amount such that when diluted 1:10 with water the formulation has a pH value of about 3 to 5.

2. A formulation according to claim 1, which when diluted 1:10 with water has a pH value of about 4.

3. A process for stabilizing a formulation of febantel in a water-miscible organic diluent comprising incorporating into the formulation so much of an acid, base or buffer salt to bring the pH to about 3 to 5 upon dilution 1:10 with water.

4. In the use of an anthelmintic comprising the steps of formulating febantel in an organic water-miscible organic diluent, storing the solution, adding water and administering the formulation, the improvement which comprises incorporating in the formulation prior to storage an amount of an acid, base or buffer salt such that upon dilution 1:10 with water the pH will be about 3 to 5, the formulation prior to addition of water containing 1 to 20% by weight of febantel and less than 3% of water.

5. A formulation according to claim 1, wherein the solvent is an ether-alcohol, heterocyclic compound, a sulphoxide, ester, ester-amide, benzyl alcohol or benzoate or phenylethanol.

6. A formulation according to claim 1, wherein the acid, base or buffer is ammonia, an amine, an aminoacid, an inorganic base, an inorganic acid, an organic acid, or a salt of one of the foregoing bases and acids.

7. A formulation according to claim 1, wherein the solvent is selected from the group consisting of glycerol formal, 2-dimethyl-4-oxymethyl-1,3-dioxalan, N-methyl-pyrrolidone, dimethyl sulphoxide, ethyl lactate, dimethylacetamide, benzyl alcohol, benzyl benzoate and phenylethanol, and the acid, base or buffer is selected from the group consisting of ammonia, methylamine, ethylamine, ethanolamine, diethanolamine, triethanolamine, lysine, choline, arginine, 2-amino-2-hydroxymethyl-1,3-propanediol, N-methylglucamine, NaOH, KOH, hydrochloric acid, sulphuric acid, phosphoric acid, acetic acid, propionic acid, citric acid, lactic acid, ascorbic acid, benzoic acid, salicylic acid, and salts of such bases and acids.

* * * * *